United States Patent [19]

Nelson

[11] 4,091,808

[45] May 30, 1978

[54] STRAP FOR IMMOBILIZING HUMAN LIMB DURING SURGERY

[76] Inventor: Mary E. Nelson, 10325 NE. Hancock Apt. #17, Portland, Oreg. 97220

[21] Appl. No.: 779,321

[22] Filed: Mar. 21, 1977

[51] Int. Cl.² .............................................. A61F 13/00
[52] U.S. Cl. ..................................... 128/133; 128/94; 128/DIG. 15
[58] Field of Search ........... 128/133, 134, 361, 303 R, 128/94, DIG. 15

[56] References Cited

U.S. PATENT DOCUMENTS

| 7,590 | 8/1850 | Blood | 128/31 X |
|---|---|---|---|
| 846,648 | 3/1907 | Crume | 128/31 |
| 3,706,310 | 12/1972 | Garnett | 128/94 |
| 3,812,852 | 5/1974 | Konvalin | 128/134 |

FOREIGN PATENT DOCUMENTS 145,434  2/1952  Australia ............................... 128/134

Primary Examiner—Lawrence W. Trapp
Attorney, Agent, or Firm—Chernoff & Vilhauer

[57] ABSTRACT

An interlocking strap to immobilize a human leg in a flexed position so as to permit surgery upon the knee. The strap is releasably secured to one part of the limb and, thereafter, the limb is secured and maintained in the flexed position by releasably securing the strap to a second part of the limb. The strap comprises an elongate portion of web material having two cooperative strips of fastening material sewn on its opposing major surfaces. The fastening material is curly pile loop and hook-type, self-gripping strip fasteners sold under the trademark VELCRO with the respective hook and loop strips mounted on respective faces of the overlapping strap portions to be fastened together around the parts of the flexed limb.

2 Claims, 5 Drawing Figures

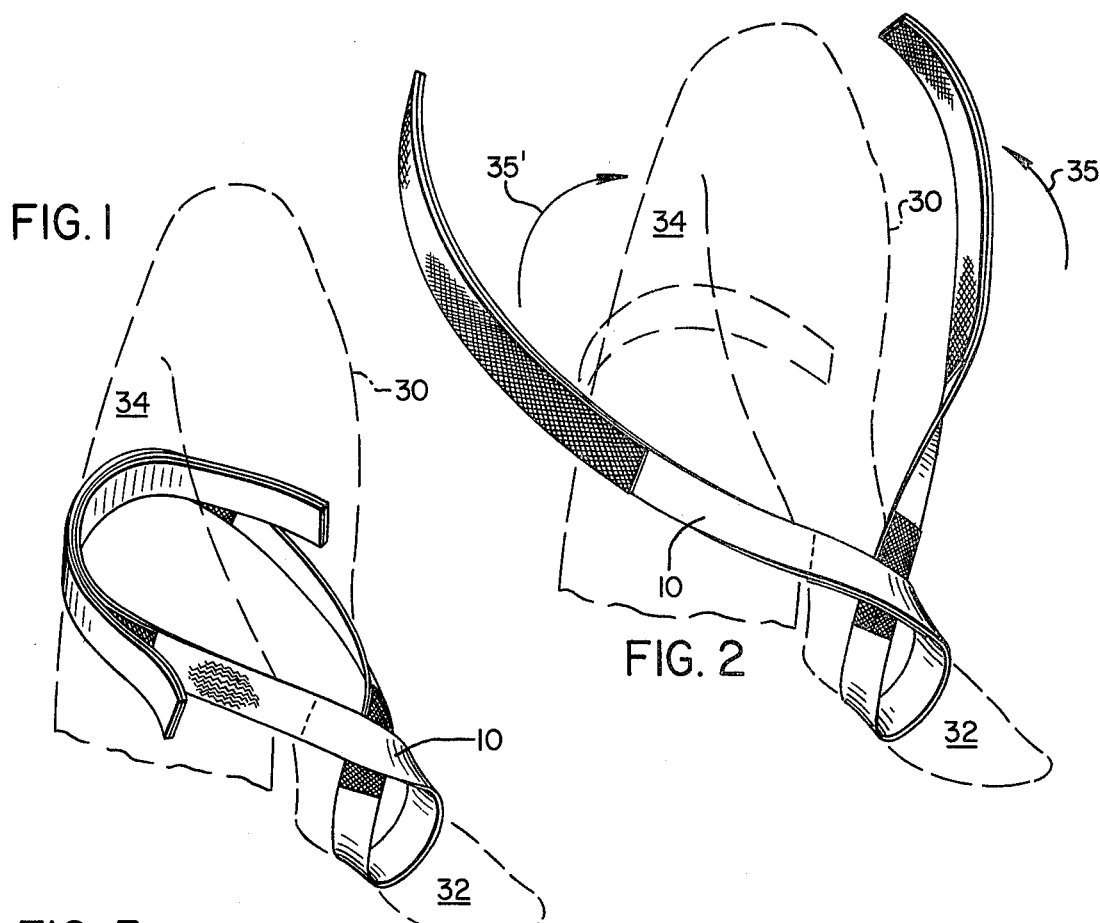
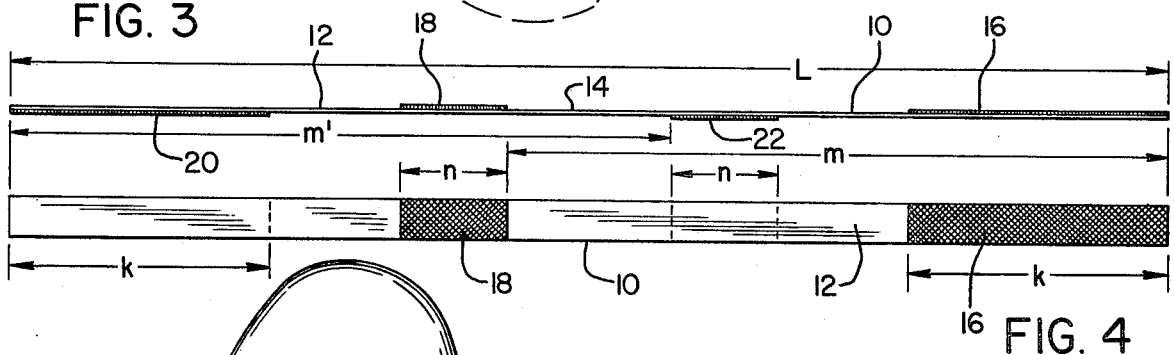
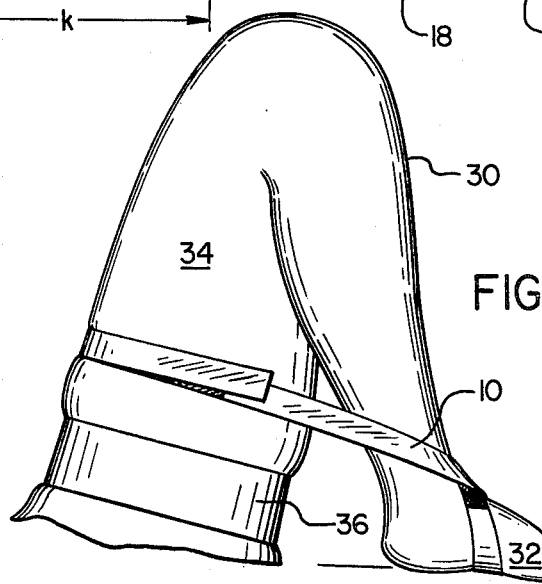

STRAP FOR IMMOBILIZING HUMAN LIMB DURING SURGERY

BACKGROUND AND SUMMARY OF THE INVENTION

The present invention relates generally to surgical procedures upon articulated body members, and more particularly relates to a restraint for immobilizing an articulated body member such as a human knee in a flexed position to permit surgery upon the hinged portion of the body member.

Surgical procedures for total knee surgery (arthoplasty) are well-known and many forms of prothesis units have been heretofore presented for replacing either or both of the femoral and tibial components of the human knee, as has been described for example in *Surgical Technique of the Mormor Modular Knee*, copyright 1973, Richards Manufacturing Company, Inc. Such surgery requires a number of hours to complete, and some method for maintaining the knee in a flexed position for extended periods of time during the various surgical procedures. Known devices and methods heretofore presented for providing such flexed restraint have failed to satisfy the criteria of such surgical procedures and, hence, have unduly complicated the overall procedure.

Known conventional restraint materials are unsatisfactory for total knee arthoplasty since, during the course of the operation, it is necessary to periodically extend and flex the patient's leg in order to perform the tasks entailed in removing and rebuilding defective parts of the knee. Thus, the use of restraint material which is not readily releaseable and reattachable would unduly prolong the operation. Further, a primary concern of such procedures is to avoid contamination of the operational site in order to obviate, if possible, any chance of infection and, hence, all materials and surgical equipment must be vigorously sanitized either by gas sterilization or autoclaving. Accordingly, the use of any restraint material which can not withstand vigorous santization is precluded by the nature of the underlying surgery. Moreover, the various steps of the operation require the leg to be sequentially flexed in a plurality of positions and; hence, any restraint material which can not be quickly adjusted is unsatisfactory.

The difficulties attendant the use of restraint materials during knee arthoplasty has generally resulted in the use of surgical team personnel to provide the prerequisite flexed restraint. However, this method is also unsatisfactory because the long periods and awkward positions required to maintain the desired immobilization tends to have an unduly fatiquing effect. More immportantly, such methods restrict the mobility of the surgical team and constitutes inefficient use of highly trained personnel.

Accordingly, it is a major objective of the present invention to provide a restraint device which can undergo both gas sterilization and autoclaving, is efficiently attachable, adjustable and removeable, and is repetitively useable in a plurality of operations to immoblize a body member such as a knee in a plurality of flexed positions.

This objective is achieved by providing an elongate web strap having a patch of curly pile looptype fabric sewn on one of its surfaces which comprises a multiplicity of projecting loops of flexible resilient threads, which are adapted to be hooked by a multiplicity of hooks projecting from a cooperative patch of curly pile hook-type fabric sewn on an opposing surface of the elongate web. This type of interlocking fabric is disclosed in U.S. Pat. Nos. 2,717,437 and 3,009,235, and is commercially available under the trademark VELCRO in the form of two cooperating tapes, which are adapted to be sewn to opposite edges of a closure for the purpose of providing a separable fastener. When the two tapes are pressed together face-to-face, a multiplicity of tiny hooks on one of the tapes engage a corresponding multiplicity of loops on the other tape, thereby causing the tapes to tenaciously cling to each other. To separate the tapes, all that is required is to grasp the ends of the tapes and pull them directly apart, which causes the hooks to yield and release the loops. Such tapes have heretofore been applied to various forms of sporting equipment to provide sportsmen with a non-slip grasp as set forth in Finney U.S. Pat. No. 3,368,811.

In the preferred embodiment of the present invention, two portions of the curly pile hook-type fabric is sewn on one surface of an elongate web strap so as to be disposed adjacent to one end and to the midportion thereof, respectively, while two portions of the curly pile loop-type material are sewn on corresponding areas of the opposing surface of the strap. In use, the strap is wrapped around the patient's foot such that the hook and loop portions adjacent and midportion are interlocked to releasably secure the strap around the foot; thereafter, the patient's leg is moved to a flexed position, and the hook and loop portions adjacent the ends of the strap are interlocked to releasably immobilize the leg in the desired flexed position. To extend the leg, all that is required is to grasp the ends of the strap and pull them directly away from the patient's leg.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is a perspective of an illustrative embodiment of the strap of the present invention as it is used to immobilize a flexed body member.

FIG. 2 depicts an illustrative method for utilizing the strap of FIG. 1 to immobilize a human leg in a flexed position.

FIG. 3 is a side view of the strap of FIG. 1 depicting the positioning of the interlocking materials upon the web material.

FIG. 4 is a bottom view of the strap of FIG. 1 depicting the positioning of the hook fabric upon the web material.

FIG. 5 is a side view of the strap of FIG. 1 deposed upon a human leg and immobilizing the leg in a partially flexed position.

DETAILED DESCRIPTION OF THE INVENTION

FIGS. 1-5 show an illustrative embodiment of the present invention wherein 10 is an elongate member of flexible fabric web material cut to a predetermined length L having a top and bottom major surface 12 and 14, respectively and faced with sheet material of special character, hereinafter more fully described, which has the property of clinging tenaciously together when pressed face to face.

A first and second portion 16 and 18 of fabric base material are sewn on the top surface 12 of the web member 10, with the first portion 16 proximate one end of the top surface, and with the second portion 18 adjacent the midportion of the top surface. The first and second portions 16 and 18 have a multiplicity of loops projecting outwardly therefrom of flexible plastic filaments. A third and fourth portion 20 and 22 of corresponding fabric base material are sewn on the bottom surface 14 of the web member 10, with the third portion 20 proximate one end of the bottom surface 14 opposite the first portion 16, and with the fourth portion 22 adjacent the midportion of the bottom surface 14 opposite of and offset from the second portion 18. The third and fourth portions 20 and 22 have a multiplicity of hooks projecting outwardly of flexible resilient plastic filaments which constitute the interlocking hooking elements and are adapted to releasably engage the multiplicity of loops on the first and second portions 16 and 18 respectively. This type of interlocking curly pile hook and loop-type of fastener material is commercially available under the trademark VELCRO in the form of two cooperating tapes which are adapted to be sewn on the fabric web material.

For adult patients, the length L of the web member is preferably 59 inches (1.5 meters) long and 1.5 inches (3.8 cm) wide. The portions of fabric base materials 16–22 have a comparable width, with the first and third portions 16 and 20 having a preferable length k of 14 inches (35 cm), and with the second and fourth portions 18 and 22 having a preferable length n of 4.5 inches (11.5 cm). The second portion 18 is preferably spaced from the first portion 16 by a distance m of 20 inches (51 cm), and the fourth portion 22 is preferably spaced from the third portion 20 by a distance m' of 19.5 inches (49.5 cm). It is important to note however, that these dimensions reflect areas which would be overlappingly interlocked when the strap is engaging the foot and thigh of the typical patient, as will hereinafter be more fully described. Some adjustment of these dimensions may be required for small adults and teenagers as well as exceptionally large persons. In any case, however, it is important to limit the fabric base materials to those areas on the web member which are likely to be overlappingly interlocked so as to minimize its bulk, achieve optimum handleability, and prevent such items as sponges, drapes, sutures and the like from adhering to exposed fabric base material.

Referring particularly to FIGS. 1, 2 and 5, after the patient's leg has been properly prepped for surgery, the midportion of the web member 10 is placed with its bottom surface 14 against the bottom arch portion of the patient's foot 32 and, thereafter, the web member 10 is wrapped snugly around the patient's foot 32 such that the fourth portion 22 criss-crosses over the second portion 18. The fourth portion 22 is then pressed down face-to-face upon the second portion 18 causing its multiplicity of hooks to releasably engage the multiplicity of loops of the second portion 18 thereby snugly securing the web member 10 to the patient's foot 32.

Once the web member 10 is snugly secured to the patient's foot, pressure is applied to both of the free ends of the web member in the directions indicated by arrows 35 and 35' such that the patient's leg is flexed to the desired flex position and; thereafter, the free ends are wrapped around the patient's thigh 34 below the tourniquet 36 such that the third portion 20 is pressed down against the first portion 16 engaging the multiplicity of loops of the first portion. Thereafter, any inadvertent attempt to move the patient's leg 30 from this flexed position to an extended position will cause the hooks and loops to tenaciously grip each other and, hence, the patient's leg is securely immobilized in the desired flexed position.

As the surgical procedures advance to a point where it is necessary to extend the patient's leg 30, the web member may be easily slipped off of the leg since it does not adhere thereto. Alternatively, the web member 10 is easily released, simply by pulling the ends directly away from each other and, hence, the web member is freely adaptable to secure the patient's leg in a plurality of flexed positions.

When the surgical procedure is completed, the web member 10 is easily removed and may be cleansed in any conventional manner. Since the web member is fully launderable and is capable of undergoing numerous sterilization processes, such as gas sterilization and autoclaving, it is repetively useable in a plurality of operations.

Although the interlocking strap has been described as including a web member 10 having fabric base material sewn thereon, it is important to note that, an alternative embodiment could fasten the hook and loop materials to any flexible material having suitable strength characteristics and in any conventional manner that can withstand conventional laundering and autoclaving.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow:

What is claimed is:

1. A strap for restraining a human leg in a flexed position during surgery upon the knee portion thereof so as to prevent the leg from extending and yet to permitting its rapid release for the purpose of extending and flexing the limb as and when required, said strap comprising:

(a) an elongate strip of flexible material having a top and bottom surface and being adapted for forming into a first closeable loop around the foot portion of the leg and a second closeable loop around the thigh of the leg so as to releasably maintain said foot and thigh in a close associative relationship during surgery upon the knee portion thereof;

(b) first closure means disposed on said top and bottom surfaces of said strip, adjacent the midportion thereof, for releasably closing said first loop when positioned around said foot, said first closure means providing said first loop with a periphery of continuously adjustable length; and (c) second closure means disposed on said top and bottom surfaces of said strip, adjacent the ends thereof, for releasably closing said second loop when positioned around said thigh, said second closure means providing said second loop with a periphery of continuously adjustable length.

2. The strap of claim 1 wherein said first and second closure means comprise first and second corresponding portions of curly pile hook and loop-type material fastened to said strip on said top and bottom surfaces, respectively, said first corresponding portions being positioned on said strip adjacent said midportion thereof and said second corresponding portions being positioned on said strip adjacent said ends thereof, said hook-type material releasably engaging said loop-type material when overlapped and pressed together and thereafter tenaciously clinging thereto along said overlapped portions of said strap.

* * * * *